United States Patent
Wales et al.

(10) Patent No.: US 7,111,769 B2
(45) Date of Patent: Sep. 26, 2006

(54) SURGICAL INSTRUMENT INCORPORATING AN ARTICULATION MECHANISM HAVING ROTATION ABOUT THE LONGITUDINAL AXIS

(75) Inventors: Kenneth S. Wales, Mason, OH (US); Douglas B. Hoffman, Harrison, OH (US); Frederick E. Shelton, IV, Hillsboro, OH (US); Jeffrey S. Swayze, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 13 days.

(21) Appl. No.: 10/615,973

(22) Filed: Jul. 9, 2003

(65) Prior Publication Data

US 2005/0006434 A1    Jan. 13, 2005

(51) Int. Cl.
*A61B 17/64* (2006.01)
(52) U.S. Cl. .............................. 227/178.1; 227/175.1; 227/180.1
(58) Field of Classification Search ............. 227/19, 227/176.1, 180.1, 175.1, 179.1, 20, 178.1; 606/146; 600/205, 146
See application file for complete search history.

(56) References Cited

U.S. PATENT DOCUMENTS

| | | | |
|---|---|---|---|
| 1,677,337 A * | 7/1928 | Grove ......................... | 606/180 |
| 5,289,963 A * | 3/1994 | McGarry et al. ......... | 227/175.1 |
| 5,312,023 A * | 5/1994 | Green et al. .............. | 227/175.1 |
| 5,405,344 A | 4/1995 | Williamson et al. | |
| 5,465,895 A | 11/1995 | Knodel et al. | |
| 5,553,765 A | 9/1996 | Knodel et al. | |
| 5,575,799 A * | 11/1996 | Bolanos et al. .............. | 606/139 |
| 5,673,840 A | 10/1997 | Schulze et al. | |
| 5,797,536 A * | 8/1998 | Smith et al. .............. | 227/175.1 |
| 5,797,537 A | 8/1998 | Oberlin | |
| 5,865,361 A | 2/1999 | Milliman et al. | |
| 6,250,532 B1 | 6/2001 | Green et al. | |
| 6,619,529 B1 * | 9/2003 | Green et al. .............. | 227/176.1 |
| 6,644,532 B1 | 11/2003 | Green et al. | |
| 6,786,382 B1 | 9/2004 | Hoffman | |
| 2004/0050902 A1 | 3/2004 | Green et al. | |
| 2004/0232197 A1 | 11/2004 | Shelton et al. | |
| 2005/0006429 A1 | 1/2005 | Wales et al. | |
| 2005/0006430 A1 | 1/2005 | Wales | |
| 2005/0006431 A1 | 1/2005 | Shelton et al. | |

* cited by examiner

*Primary Examiner*—Rinaldi I. Rada
*Assistant Examiner*—Paul Durand

(57) ABSTRACT

A surgical instrument particularly suited to endoscopic articulates an end effector by including an end effector having a geared articulation mechanism that converts rotational motion from a handle portion. A hollow articulation drive tube transfers the rotation motion in some versions to a spear gear, bevel gear or snaggle tooth gear articulation mechanism. Alternatively, one or more threaded drive rod offset from a longitudinal axis engages a worm gear or flex-neck articulation mechanism.

8 Claims, 16 Drawing Sheets

SURGICAL INSTRUMENT INCORPORATING AN ARTICULATION MECHANISM HAVING ROTATION ABOUT THE LONGITUDINAL AXIS

CROSS REFERENCE TO RELATED APPLICATIONS

The present application is related to four co-pending and commonly-owned applications filed on even date herewith, the disclosure of each is hereby incorporated by reference in their entirety, these four applications being respectively entitled:

(1) "SURGICAL STAPLING INSTRUMENT INCORPORATING A TAPERED FIRING BAR FOR INCREASED FLEXIBILITY AROUND THE ARTICULATION JOINT" to Frederick E. Shelton IV, Mike Setser, and Bruce Weisenburgh;

(2) "SURGICAL STAPLING INSTRUMENT INCORPORATING AN ARTICULATION JOINT FOR A FIRING BAR TRACK" to Douglas B. Hoffman;

(3) "SURGICAL STAPLING INSTRUMENT HAVING ARTICULATION JOINT SUPPORT PLATES FOR SUPPORTING A FIRING BAR" to Kenneth S. Wales and Joseph Charles Hueil; and (4) "A SURGICAL INSTRUMENT WITH A LATERAL-MOVING ARTICULATION CONTROL" to Kenneth S. Wales.

FIELD OF THE INVENTION

The present invention relates in general to surgical instruments that are suitable for endoscopically inserting an end effector (e.g., endocutter, grasper, cutter, staplers, clip applier, access device, drug/gene therapy delivery device, and a energy device using ultrasound, RF, laser, etc.) to a surgical site, and more particularly to such surgical instruments with an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue engage tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Positioning the end effector is constrained by the trocar. Generally these endoscopic surgical instruments include a long shaft between the end effector and a handle portion manipulated by the clinician. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

More recently, U.S. Pat. Ser. No. 10/443,617, "SURGICAL STAPLING INSTRUMENT INCORPORATING AN E-BEAM FIRING MECHANISM" to Shelton et al., filed on 20 May 2003, describes an improved "E-beam" firing bar for severing tissue and actuating staples. Some of the additional advantages include affirmatively spacing the jaws of the end effector, even if slightly too much or too little tissue is clamped for optimal staple formation. Moreover, the E-beam firing bar engages the end effector and staple cartridge in a way that enables several beneficial lockouts to be incorporated.

Depending upon the nature of the operation, it may be desirable to further adjust the positioning of the end effector of an endoscopic surgical instrument. In particular, it is often desirable to orient the end effector at an axis transverse to the longitudinal axis of the shaft of the instrument. The transverse movement of the end effector relative to the instrument shaft is conventionally referred to as "articulation". This articulated positioning permits the clinician to more easily engage tissue is some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation.

While these longitudinally controlled articulation mechanisms have provided certain advantages to surgical instruments such as for endoscopic stapling and severing, it is believed that an alternative articulation motion would provide additional design flexibility.

U.S. Pat. No. 5,405,344 teaches an endoscopic surgical instrument that, in the embodiment (shown in FIGS. 7–13), uses rotary motion about the longitudinal axis to articulate the end effector of the instrument in a conical motion. As taught, the articulating end effector uses a ball (convex member 174) attached to the end effector and a socket in a distal end of the hollow support tube 162. A hollow shaft 188 is bent into a "Z" shape and has a distal portion 198 that is bent to form at an angle to the longitudinal axis. Distal portion 198 is rotatably mounted within a passageway 178 extending into the ball or convex member 174 of the end effector. When the distal portion 198 is bent to the same angle as the passageway 178, the end effector and hollow shaft 188 can be assembled (in one position) aligning the longitudinal axis of the end effector with the hollow shaft 188. Rotation of the hollow shaft 188 from this alignment position articulates the end effector in a conical motion. As shown in FIGS. 10–13, the end effector both translates and rotates relative to the longitudinal axis. While providing articulation, the conical motion is not intuitive and requires rotation and repositioning of the surgical instrument to align the end effector with the tissue at a surgical site. What is needed is an articulation mechanism that can use rotation to articulate the end effector from side to side within a single plane relative to the longitudinal axis of the surgical instrument.

Consequently, a significant need exists for an articulating surgical instrument that incorporates an articulation mechanism that responds to a control motion other than a longitudinal translation.

BRIEF SUMMARY OF THE INVENTION

The invention overcomes the above-noted and other deficiencies of the prior art by providing a surgical instrument particularly suited to use through a trocar cannula passageway for endoscopic and laparoscopic clinical procedures In one aspect of the invention, a surgical instrument has a handle portion that produces an actuating motion and a rotational motion that are transferred through a shaft to an end effector that is responsive to the actuating motion and to an articulation mechanism that is responsive in a geared fashion to the rotational motion. The articulation mechanism articulates the end effector from the longitudinal axis of the shaft so that the end effector may more effectively reach a surgical site and perform a diagnostic or therapeutic treatment by being actuated.

In another aspect of the invention, a surgical instrument has a handle portion that produces a rotational motion that is transferred down a shaft. In particular, the shaft includes an articulation drive tube that is rotated by the rotational motion and that encompasses a frame. A gear section distally projecting about at least a portion of a circumference of a distal end of the articulation drive tube engages a spur gear on a pivot axis between the shaft and an end effector, converting the rotational motion of the articulation drive tube to an articulation motion pivoting the end effector from a longitudinal axis of the shaft. The hollow articulation drive tube creates an interior space suitable for incorporating various structures to communicate between the handle portion and the end effector, providing additional design options for various types of surgical instruments.

In yet another aspect of the invention, a surgical instrument has a handle portion that produces a rotational motion. A shaft with a longitudinal axis includes an elongate frame attached to the handle portion and an articulation drive tube offset from the longitudinal axis of the shaft. The articulation drive tube is responsive to the rotational motion and includes a distal, exterior threaded portion. An end effector is distally and pivotally coupled to the frame at a pivot axis. A gear connection offset from the pivot axis and the longitudinal axis of the shaft engages the distal, exterior threaded portion of the articulation drive tube to convert the rotational motion of the articulation drive tube to an articulation motion pivoting the end effector from the longitudinal axis of the shaft.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
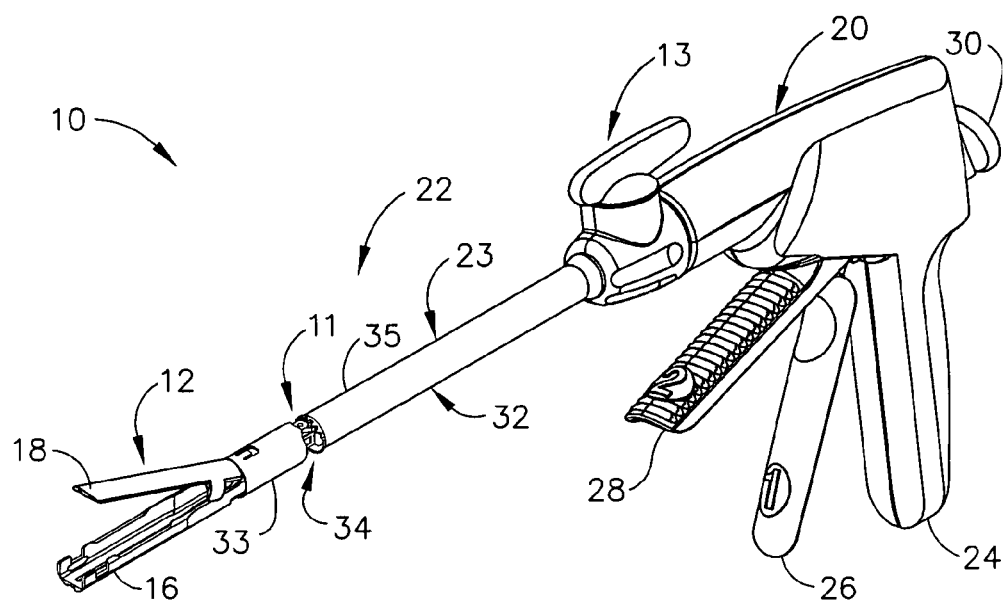
FIG. 1 is a perspective view of an articulating surgical instrument in a nonarticulated position.
Figure 2:
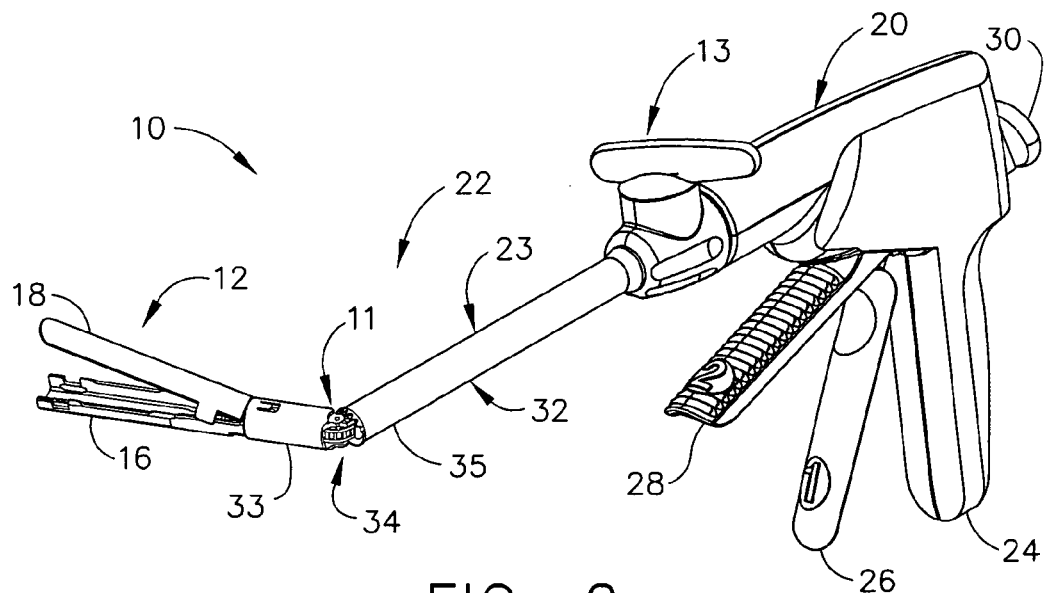
FIG. 2 is a perspective view of an articulating surgical instrument in an articulated position.
Figure 3:
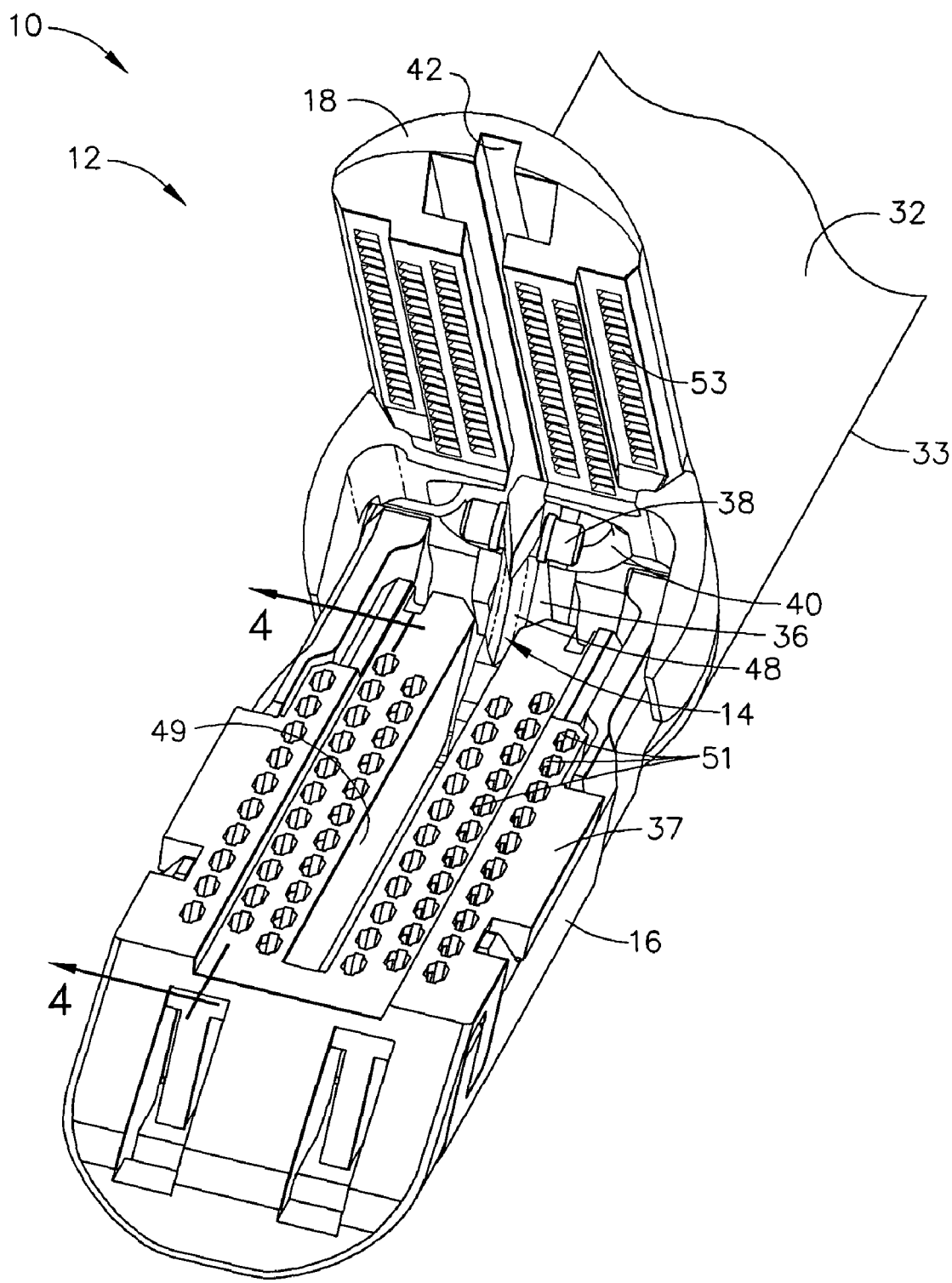
FIG. 3 is a perspective view of an opened end effector of the articulating surgical instrument of FIGS. 1–2.

Turning to the Drawings, wherein like numerals denote like components throughout the several views, FIGS. 1–3 depict a surgical instrument, which in the illustrative embodiment is more particularly a surgical stapling and severing instrument 10, that is capable of practicing the unique benefits of the present invention. In particular, the surgical stapling and severing instrument 10 is sized for insertion, in a nonarticulated state as depicted in FIG. 1, through a trocar cannula passageway to a surgical site in a patient for performing a surgical procedure. Once an articulation mechanism 11 and a distally attached end effector 12 are inserted through the cannula passageway, the articulation mechanism 11 may be remotely articulated, as depicted in FIG. 2, by an articulation control 13. Thereby, the end effector 12 may reach behind an organ or approach tissue from a desired angle or for other reasons. For instance, a firing mechanism, advantageously depicted as an E-beam firing bar 14 (depicted in FIG. 3), that severs clamped tissue, engages an elongate channel 16 and a pivotally attached anvil 18.

The surgical and stapling and severing instrument 10 includes a handle portion 20 connected to an implement portion 22, the latter further comprising a shaft 23 distally terminating in the articulating mechanism 11 and the end effector 12. The handle portion 20 includes a pistol grip 24 toward which a closure trigger 26 is pivotally drawn by the clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12. Thereafter, a release button 30 is depressed to release the clamped tissue.

An outmost closure sleeve 32 of the shaft 23 longitudinally translates in response to the closure trigger 26 to pivotally close the anvil 18. Specifically, a distal portion, or closure ring 33, of the closure sleeve 32 with respect to the articulation mechanism 11 is indirectly supported by a frame 34 of the implement portion 22 (partially visible at the articulation mechanism 11). At the articulation mechanism 11, a proximal portion, or closure tube 35, of the closure sleeve 32 communicates with the distal portion (closure ring) 33. The frame 34 is flexibly attached to the elongate channel 16 via the articulation mechanism 11, enabling articulation in a single plane. The frame 34 also longitudinally slidingly supports a firing drive member 36 that communicates a firing motion from the firing trigger 28 to the firing bar 14. Only the firing bar 14 of the firing drive member 36 is depicted FIG. 3, but the firing drive member 36 is described below further detail with regard to various versions of a rotationally controlled articulation mechanism 11.

It will be appreciated that the terms "proximal" and "distal" are used herein with reference to a clinician gripping a handle of an instrument. Thus, the end effector 12 is distal with respect to the more proximal handle portion 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

E-beam Firing Bar

Figure 4:
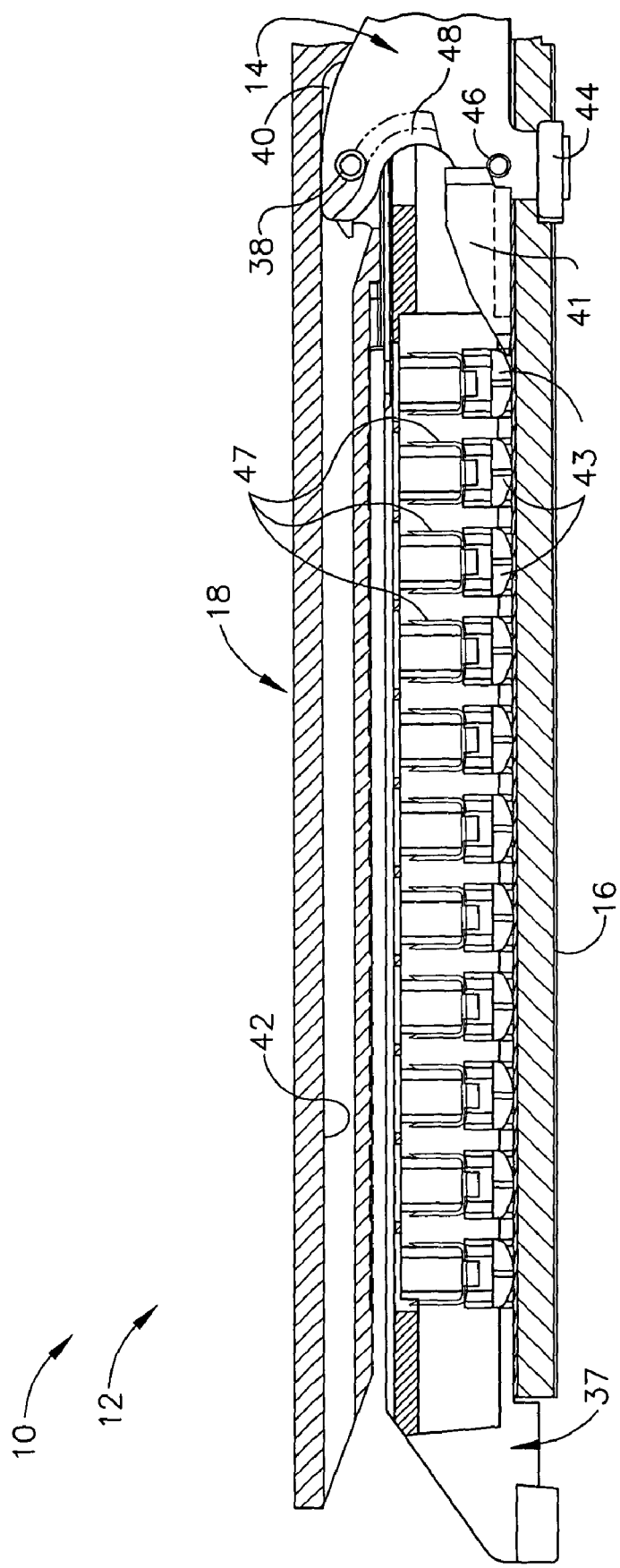
FIG. 4 depicts a side elevation view in section of the end effector of FIG. 3, the section generally taken along lines 4—4 of FIG. 3 to expose portions of a staple cartridge but also depicting the firing bar along the longitudinal centerline.
Figure 5:
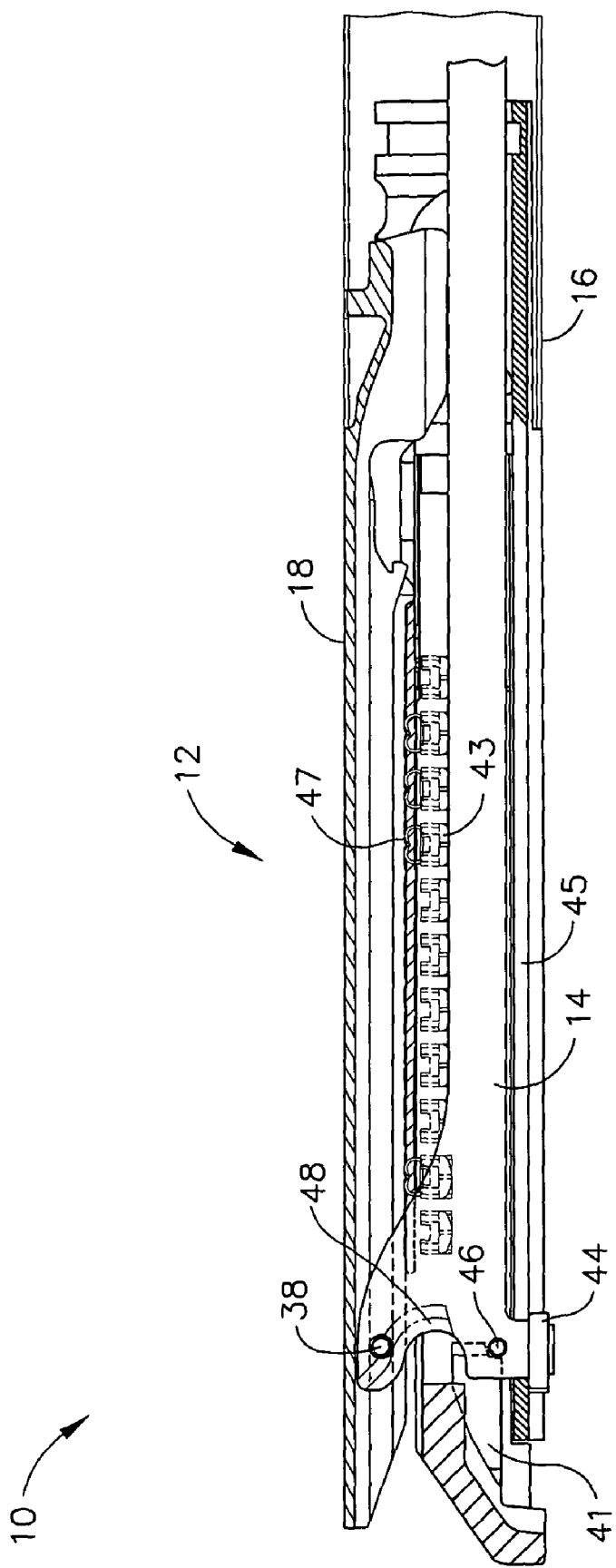
FIG. 5 depicts a side elevation view in section of the end effector of FIG. 4 after the firing bar has fully fired.

FIGS. 3–5 depict the end effector 12 employing the E-beam firing bar 14 to perform a number of functions. In FIG. 3, the firing bar 14 is proximally positioned, allowing an unspent staple cartridge 37 to be installed into the elongate channel 16. In particular, an upper pin 38 of the firing bar 14 resides within a recess, depicted as an anvil pocket 40 allowing the anvil 18 to be repeatedly opened and closed. With the end effector closed as depicted in FIG. 4, the firing bar 14 is advanced in engagement with the anvil 18 by having the upper pin 38 enter a longitudinal anvil slot 42. A lower most pin, or firing bar cap 44, engaged a lower surface of the elongate channel 16 by having the firing bar 14 extend through a channel slot 45. A middle pin 46 slidingly engages a top surface of the elongate channel 16, cooperating with the firing bar cap 44. Thereby, the firing bar 14 affirmatively spaces the end effector 12 during firing, overcoming pinching that may occur with a minimal amount of clamped tissue and overcoming staple malformation with an excessive amount of clamped tissue.

During firing, a distally presented cutting edge 48 between the upper pin 38 and middle pin 46 of the firing bar enters a proximally presented vertical slot 49 of the staple cartridge 37, severing tissue clamped between the staple cartridge 37 and the anvil 18. As shown in FIG. 4, the middle pin 46 actuates the staple cartridge 37 by entering into a firing slot within the staple cartridge 37, driving a wedge sled 41 into upward camming contact with staple drivers 43 that in turn drive a plurality of staples 47 out of staple apertures 51 in the staple cartridge 37 into forming contact with staple pockets 53 on an inner surface of the anvil 18. FIG. 5 depicts the firing bar 14 fully distally translated after completing severing and stapling tissue.

Two-axis Handle

Figure 6:
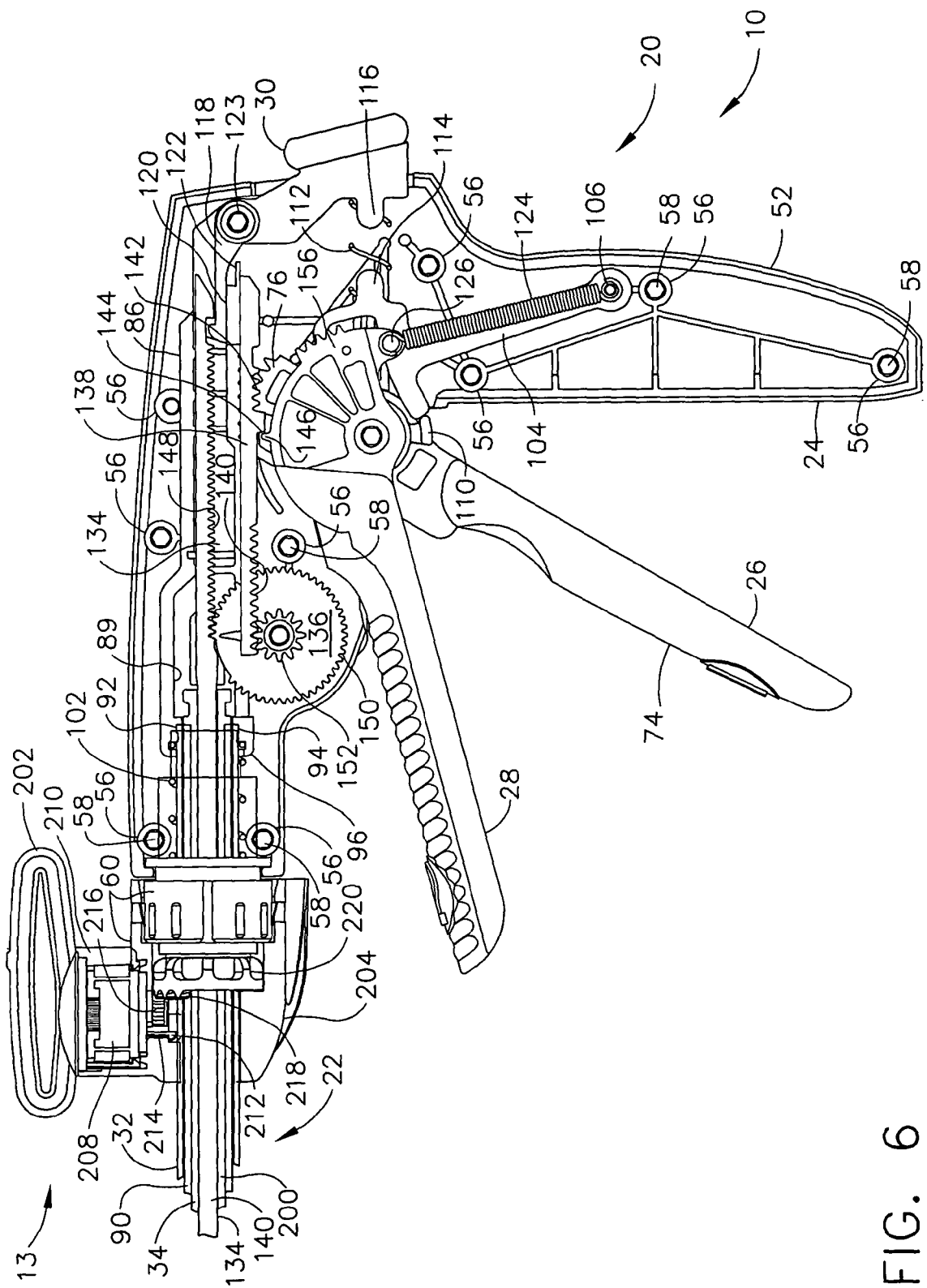
FIG. 6 depicts a side elevation view in section of a handle portion of a proximal end of the surgical instrument of FIG. 1 including a rotating articulation control.
Figure 7:
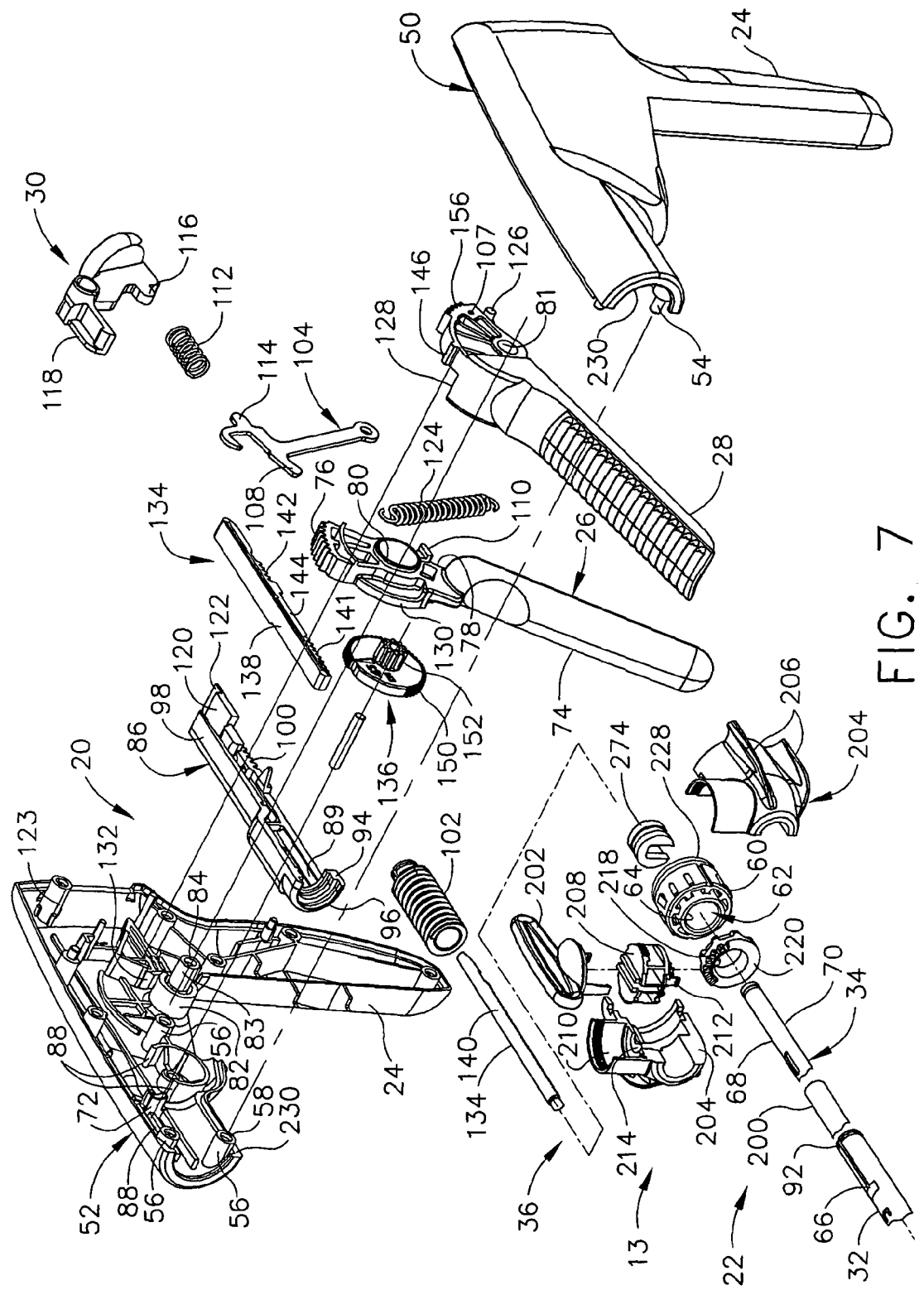
FIG. 7 depicts a perspective, exploded view of the handle portion of the proximal end of the surgical instrument of FIG. 1.
Figure 8:
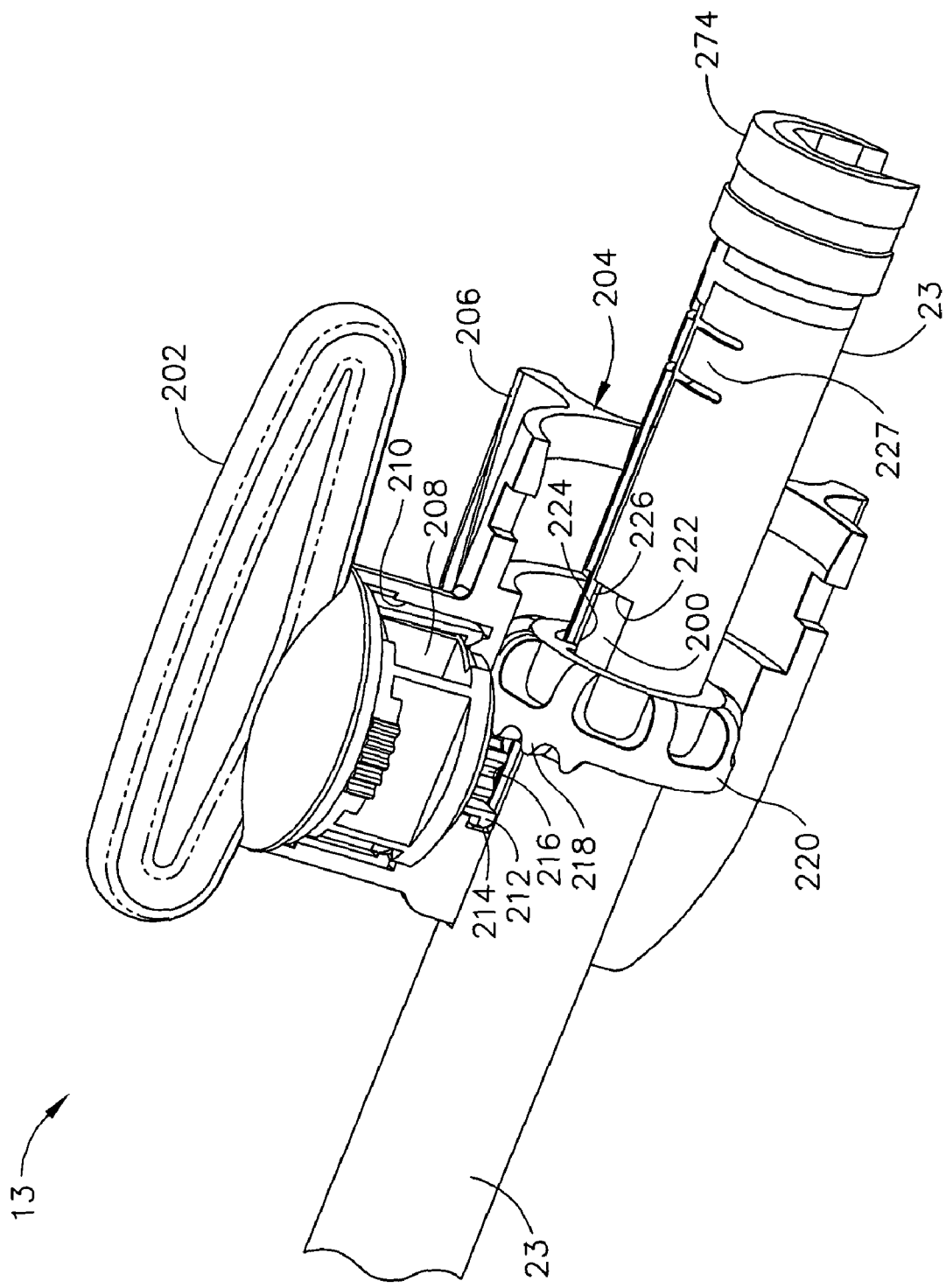
FIG. 8 depicts a perspective view looking downward, forward and to the right of a distal portion of the handle portion of the surgical instrument of FIG. 1 partially cutaway to expose a rotating articulation control mechanism.
Figure 9:
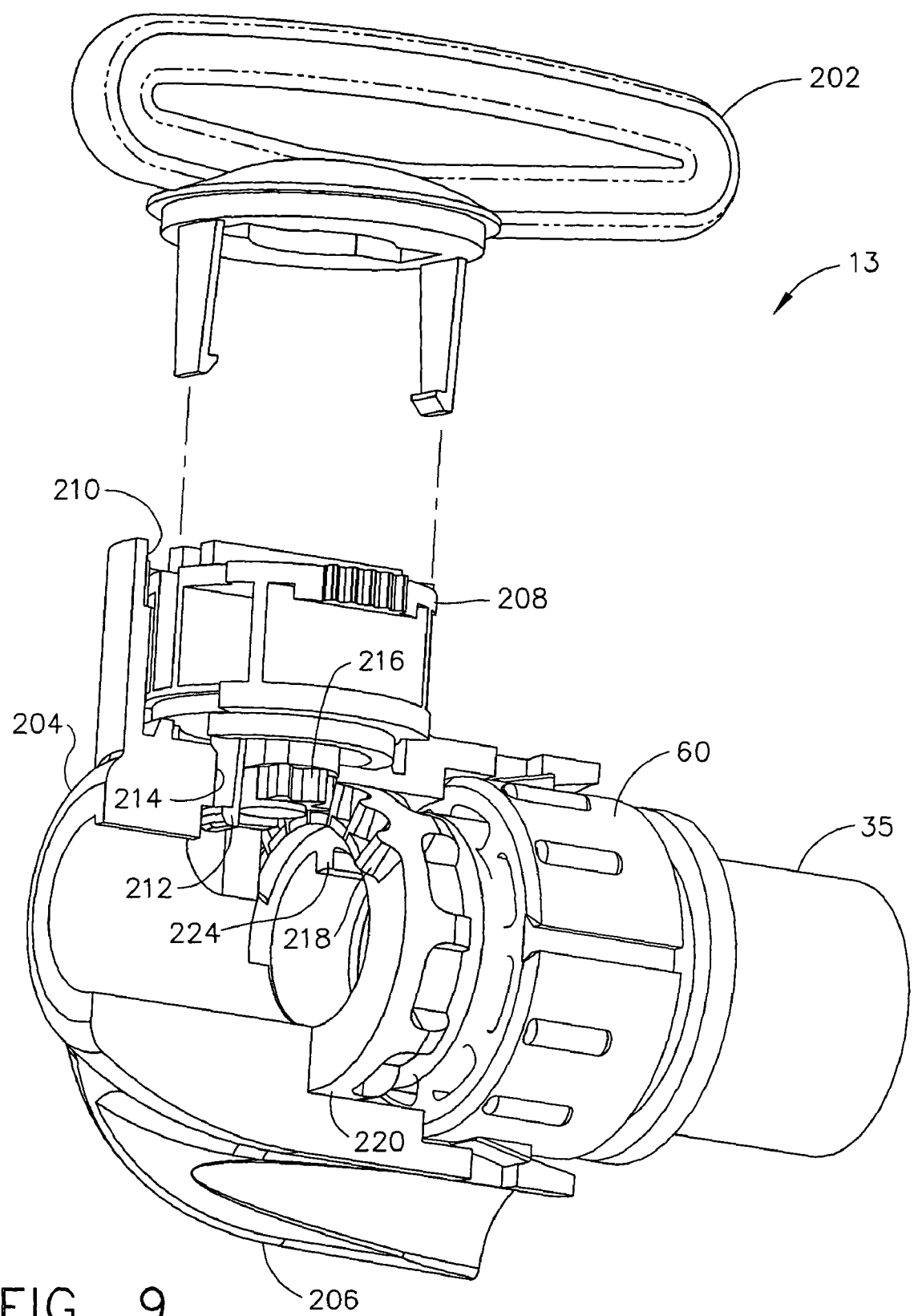
FIG. 9 depicts a perspective view looking upward, rearward and to the right of the distal portion of the handle portion of FIG. 8, partially cutaway to expose the rotating articulation control mechanism and have a rotating articulation control knob disassembled.

With reference to FIGS. 6–7, the handle portion 20 is comprised of first and second base sections 50 and 52, which are molded from a polymeric material such as a glass-filled polycarbonate. The first base section 50 is provided with a plurality of cylindrical-shaped pins 54. The second base section 52 includes a plurality of extending members 56, each having a hexagonal-shaped opening 58. The cylindrical-shaped pins 54 are received within the hexagonal-shaped openings 58 and are frictionally held therein for maintaining the first and second base sections 50 and 52 in assembly.

A housing cap 60 has a bore 62 extending completely through it for engaging and rotating the implement portion 22 about its longitudinal axis. The housing cap 60 includes an inwardly protruding boss 64 extending along at least a portion of the bore 62. The protruding boss 64 is received within a longitudinal slot 66 formed at a proximal portion of the closure sleeve 32 such that rotation of the housing cap 60 effects rotation of the closure sleeve 32. It will be appreciated that the boss 64 further extends through frame 34 and into contact with a portion of the firing drive member 36 to effect their rotation as well. Thus, the end effector 12 (not shown in FIGS. 3–4) rotates with the housing cap 60.

A proximal end 68 of the frame 34 passes proximally through the housing cap 60 and is provided with a circumferential notch 70 that is engaged by opposing channel securement members 72 extending respectively from the base sections 50 and 52. Only the channel securement member 72 of the second base section 52 is shown. The channel securement members 72 extending from the base sections 50, 52 serve to secure the frame 34 to the handle portion 20 such that the frame 34 does not move longitudinally relative to the handle portion 20.

The closure trigger 26 has a handle section 74, a gear segment section 76, and an intermediate section 78. A bore 80 extends through the intermediate section 78. A cylindrical support member 82 extending from the second base section 52 passes through the bore 80 for pivotally mounting the closure trigger 26 on the handle portion 20. A second cylindrical support member 83 extending from the second base section 52 passes through a bore 81 of firing trigger 28 for pivotally mounting on the handle portion 20. A hexagonal opening 84 is provided in the cylindrical support member 83 for receiving a securement pin (not shown) extending from the first base section 50.

A closure yoke 86 is housed within the handle portion 20 for reciprocating movement therein and serves to transfer motion from the closure trigger 26 to the closure sleeve 32. Support members 88 extending from the second base section 52 and securement member 72, which extends through a recess 89 in the yoke 86, support the yoke 86 within the handle portion 20.

A proximal end 90 of the closure sleeve 32 is provided with a flange 92 that is snap-fitted into a receiving recess 94 formed in a distal end 96 of the yoke 86. A proximal end 98 of the yoke 86 has a gear rack 100 that is engaged by the gear segment section 76 of the closure trigger 26. When the closure trigger 26 is moved toward the pistol grip 24 of the handle portion 20, the yoke 86 and, hence, the closure sleeve 32 move distally, compressing a spring 102 that biases the yoke 86 proximally. Distal movement of the closure sleeve 32 effects pivotal translation movement of the anvil 18 distally and toward the elongate channel 16 of the end effector 12 and proximal movement effects closing, as discussed below.

The closure trigger 26 is forward biased to an open position by a front surface 130 interacting with an engaging surface 128 of the firing trigger 28. Clamp first hook 104 that pivots top to rear in the handle portion 20 about a pin 106 restrains movement of the firing trigger 28 toward the pistol grip 24 until the closure trigger 26 is clamped to its closed position. Hook 104 restrains firing trigger 28 motion by engaging a lockout pin 107 in firing trigger 28. The hook 104 is also in contact with the closure trigger 26. In particular, a forward projection 108 of the hook 104 engages a member 110 on the intermediate section 78 of the closure trigger 26, the member 110 being outward of the bore 80 toward the handle section 74. Hook 104 is biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30.

As the yoke 86 moves distally in response to proximal movement of the closure trigger 26, an upper latch arm 118 of the release button 30 moves along an upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position.

The latch arm 118 can be moved out of the recess 122 to release the anvil 18 by pushing the release button 30 inward. Specifically, the upper latch arm 118 pivots upward about pin 123 of the second base section 52. The yoke 86 is then permitted to move proximally in response to return movement of the closure trigger 26.

A firing trigger return spring 124 is located within the handle portion 20 with one end attached to pin 106 of the second base section 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28 biasing front surface 130 of closure trigger 26.

As the closure trigger 26 is moved toward the pistol grip 24, its front surface 130 engages with the engaging surface 128 on the firing trigger 28 causing the firing trigger 28 to move to its "firing" position. When in its firing position, the firing trigger 28 is located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 extends from the second base section 52 to prevent the closure trigger 26 from rotating beyond its initial position.

The surgical stapling and severing instrument 10 additionally includes a reciprocating section 134, a multiplier 136 and a drive member 138. The reciprocating section 134 comprises a wedge sled, or wedge sled, in the implement portion 22 (not shown in FIG. 6–7) and a metal drive rod 140.

The drive member 138 includes first and second gear racks 141 and 142. A first notch 144 is provided on the drive member 138 intermediate the first and second gear racks 141, 142. During return movement of the firing trigger 28, a tooth 146 on the firing trigger 28 engages with the first notch 144 for returning the drive member 138 to its initial position after staple firing. A second notch 148 is located at a proximal end of the metal drive rod 140 for locking the metal drive rod 140 to the upper latch arm 118 of the release button 30 in its unfired position.

The multiplier 136 comprises first and second integral pinion gears 150 and 152. The first integral pinion gear 150 is engaged with a first gear rack 154 provided on the metal drive rod 140. The second integral pinion gear 152 is engaged with the first gear rack 141 on the drive member 138. The first integral pinion gear 150 has a first diameter and the second integral pinion gear 152 has a second diameter that is smaller than the first diameter.

Rotational Articulation Control

With reference to FIGS. 6–9, the handle portion 20 advantageously incorporates the articulation control 13 that both rotates the implement portion 22 about the longitudinal axis of the surgical instrument 10 and articulates the end effector 12 to an angle with the longitudinal axis. A hollow articulation drive tube 200 is concentrically located within the closure sleeve 32 and is operably coupled to an actuation lever 202 such that rotation of actuation lever 202 rotates tube 200 about the longitudinal axis and causes perpendicular rotation or articulation of the closure ring 250 and end effector 12. This articulation of the closure ring 250 corresponds to the degree and direction of rotation of actuator lever 202 viewed and manipulated by the clinician. In the illustrative version, the relationship is one to one, with the degree of rotation of the actuator lever 202 corresponding to the degree of articulation from the longitudinal axis of the shaft 23, thus providing an intuitive indication to the clinician. It will be appreciated that other angular relationships may be selected.

The articulation control 13 includes a pair of mirrored articulation transmission housings 204 that are attached to the housing cap 60. Moreover, the articulation transmission housing 204 includes longitudinally aligned external tabs 206 that a clinician twists to effect rotation of the articulation transmission housing 204, and thus of the end effector 12, about the longitudinal axis of the implement portion 22. The actuator lever 202 is attached to a cylindrical articulation body 208 that resides within a cylindrical recess 210 opening generally upward and perpendicular to the shaft 23. The lowermost portion of the articulation body 208 includes prongs 212 that snap fit into an opening 214 in the articulation transmission housing 208 near to the shaft 23, the prongs 212 preventing the articulation body 208 from being withdrawn from the cylindrical recess 210.

Annularly presented gear teeth 216 are located about the lower portion of the articulation body 208 and mesh with teeth 218 on an articulation yoke 220. The articulation yoke 220 straddles an articulation rectangular window 222 formed in the closure sleeve 32. Closure sleeve 32 is slidably moveable within the articulation control 13 (in the longitudinal direction) to close and open the end effector 12. The articulation drive tube 200 moves longitudinally with the closure sleeve 32 relative to the fixed articulation control 13. Window 222 provides clearance for a boss 224 inwardly presented from the articulation yoke 220 that passes through the rectangular window 222 to engage a slot 226 in the articulation drive tube 200, longitudinally positioning the articulation drive tube 200 for rotational motion. The hollow articulation drive tube 200 extends longitudinally within the closure sleeve 32 from the articulation mechanism 11 and terminates distally before the locking tabs 227 of the closure sleeve 32. The tabs 227 are inwardly bent behind the proximal face of the articulation drive tube 200 and thereby retaining the articulation drive tube 200 in the shaft 23.

It should be appreciated that the articulation transmission housing 204 is operatively associated to the closure tube 35 of the shaft 23. The housing cap 60 retains the articulation yoke 220 in the articulation transmission housing 204 and retains the articulation control 13 within the handle portion 20 by presenting proximally an outer diameter circular groove 228 that engages a circular inward lip 230 at the distal opening of the assembled base sections 50, 52.

Figure 10:
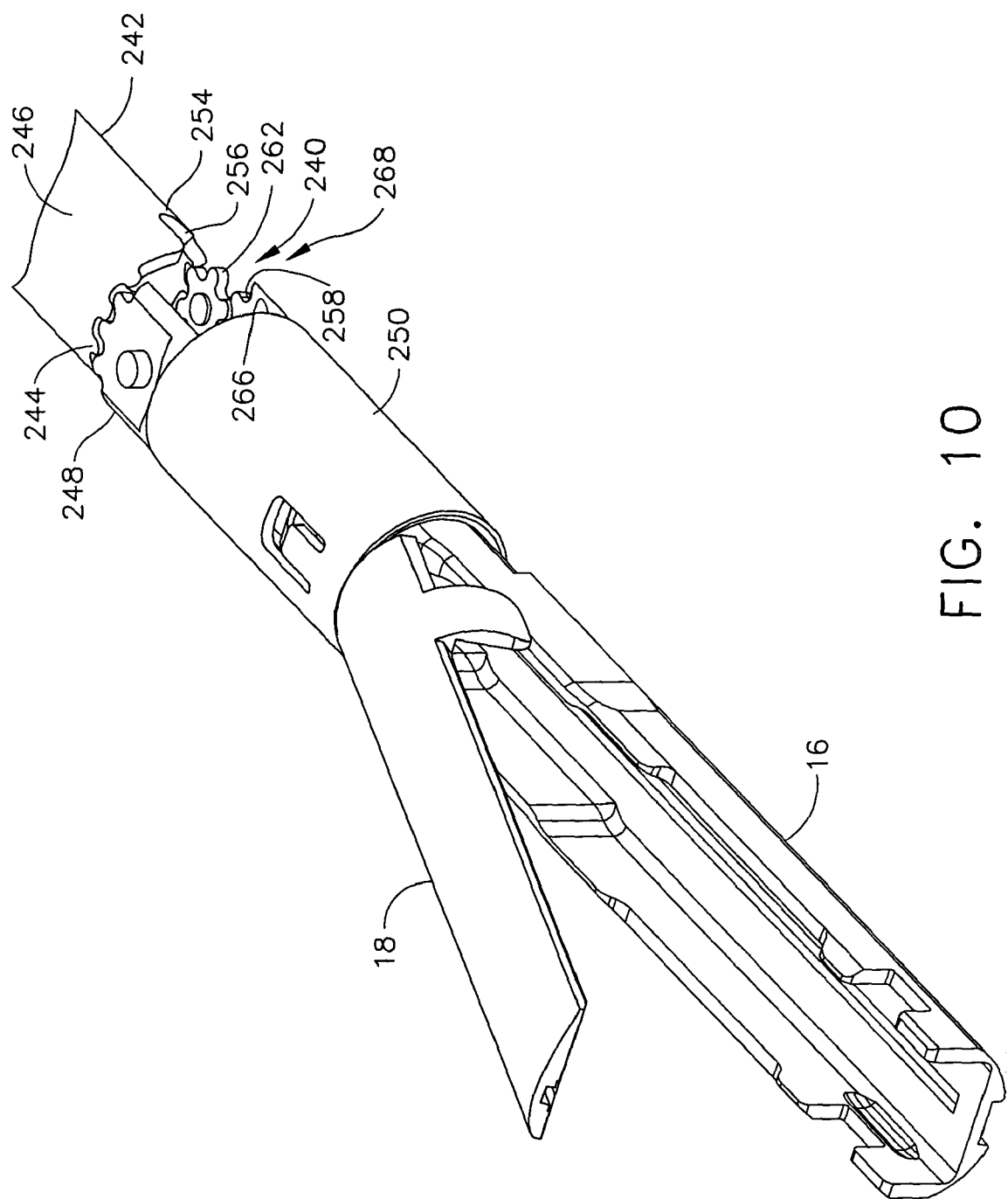
FIG. 10 depicts a top perspective detail view of a spur gear articulation mechanism and end effector of the surgical instrument of FIG. 1 with firing and frame portions removed.
Figure 11:
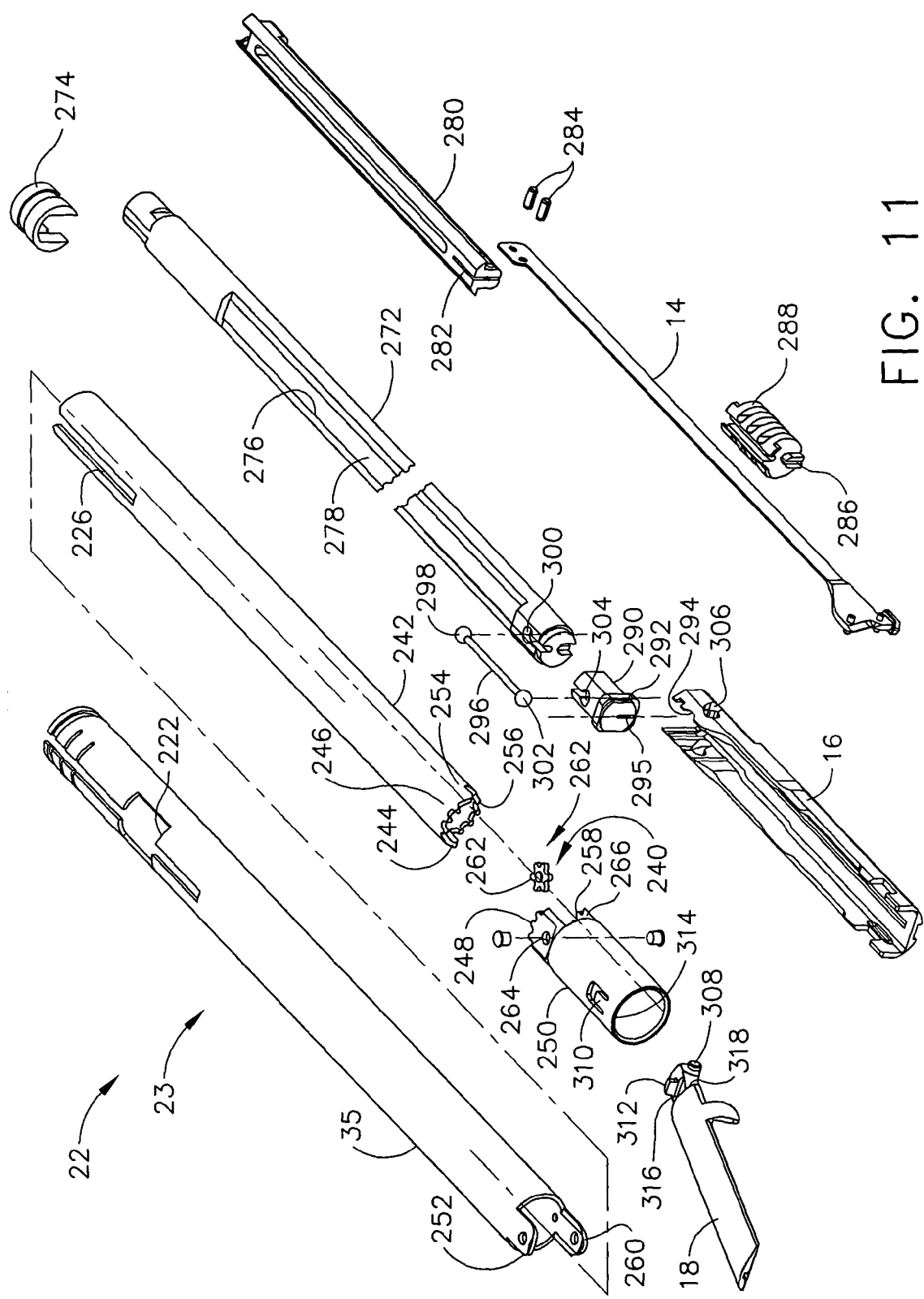
FIG. 11 depicts a perspective, exploded view of an implement portion of the surgical instrument of FIG. 1 including a spur gear articulation mechanism.

FIGS. 10 and 11 depict the gear articulation mechanism 11 of FIGS. 1–2 in the form of a spur gear articulation mechanism 240, which is generally the same as described above but with additional articulation driving components on the other side of the articulation mechanism 240 to thereby increase performance. Articulation mechanism 240 has a rotatable hollow articulation drive tube 242 that is concentrically located within closure sleeve 32 and has a distally projecting gear section 244 about a first circumference portion 246. Gear section 244 meshes with a spur gear 248 attached to and proximally projecting from closure ring 250 which pivots about pins 253 extending through first and second pivot points 252, 260 projecting distally from the closure sleeve 32. Thus, an articulation pivot axis passes through both the first and second pivot points 252, 260 and pins 253 rotatably couple closure ring 250 to the closure sleeve 32. Rotation of drive 242 engages the gears 242 and 248 and articulates closure ring 250 about first and second pivot points 252, 260.

To increase the effective surface area of gear contact between the hollow articulation drive tube 242 and the closure ring 250, a second circumference portion 254 of the hollow articulation drive tube 242 has a recessed distally projecting gear section 256 extending therefrom. Gear section 256 is operably coupled to a second spur gear 258 attached to and proximally projecting from an opposite lateral side of the closure ring 250 by a reversing gear 262 pivotally supported by the frame 34. Reversing gear 262 engages both the recessed distally projecting gear section 256 on one side and the second spur gear 258 of the closure ring 250 on the other.

When the closure trigger 26 is actuated, both the hollow articulation drive tube 242 and pivotally attached closure tube 250 of the closure sleeve 32 are moved distally to close the anvil 18. The closure tube 35 of the closure sleeve 32 is spaced away from the closure ring 33 by pivot points 252, 260 pinned to pivot holes 264 and 266 centered in spur gears 248, 258, and a frame opening 268 that extends therethrough. The frame opening 268 provides clearance so that the proximal edges of the closure ring 33 and the distal edges of the closure tube 35 of the closure sleeve 32 do not collide during articulation.

FIG. 11 depicts in disassembled form an implement portion 270 that includes the spur gear articulation mechanism 240. A frame 272 is longitudinally attachable to the handle portion 20 (depicted in FIGS. 1 and 2) with a bushing 274 on its proximal end for rotatingly engagement thereto. A frame trough 276 formed by an opening 278 longitudinally aligned with the center of the frame 272 is longer than a firing connector 280 that slides longitudinally within the frame trough 276. The proximal end of the firing connector 280 rotatingly engages the distal end of the metal drive bar 140 (depicted in FIG. 6). The distal end of the firing connector 280 includes a slot 282 that receives a proximal end of the firing bar 14, attached therein by pins 284. A more distal portion of the firing bar 14 is positioned within a lower groove 286 in a firing bar slotted guide 288 that is distally engaged with an articulating frame member 290 and the frame 272.

Articulating frame member 290 has a channel-anchoring member 292 that distally attaches to an attachment collar 294 of a proximal portion in the elongate channel 16. The firing bar 14 passes through a lower slot 295 in the articulating frame member 290. The articulating frame member 290 is spaced away from the distal end of the frame 272 by the firing bar slotted guide 288 and flexibly attached thereto for articulation by a resilient connector 296. A widened proximal end 298 of the resilient connector 296 engages a distally communicating top recess 300 in the distal end of the frame 272 and a widened distal end 302 of the resilient connector 296 engages a proximally communicating top recess 304 in the articulating frame member 290. Thereby, the elongate channel 16 is attached to the handle portion 20, albeit with a flexible portion therebetween.

The elongate channel 16 also has an anvil cam slot 306 that pivotally receives an anvil pivot 308 of the anvil 18. The closure ring 250 that encompasses the articulating frame member 290 includes a distally presented tab 310 that engages an anvil feature 312 proximate but distal to the anvil pivot 308 on the anvil 18 to thereby effect opening. When the closure ring 250 is moved forward, its distally presented closing face 314 contacts a ramped cylindrical closing face 316, which is distal to tab 312 of the anvil 18. This camming action closes the anvil 18 downward until the closing face 314 of the closure ring 250 contacts a flat cylindrical face 318 of the anvil 18.

Snaggle Tooth Articulation Mechanism

Figure 12:
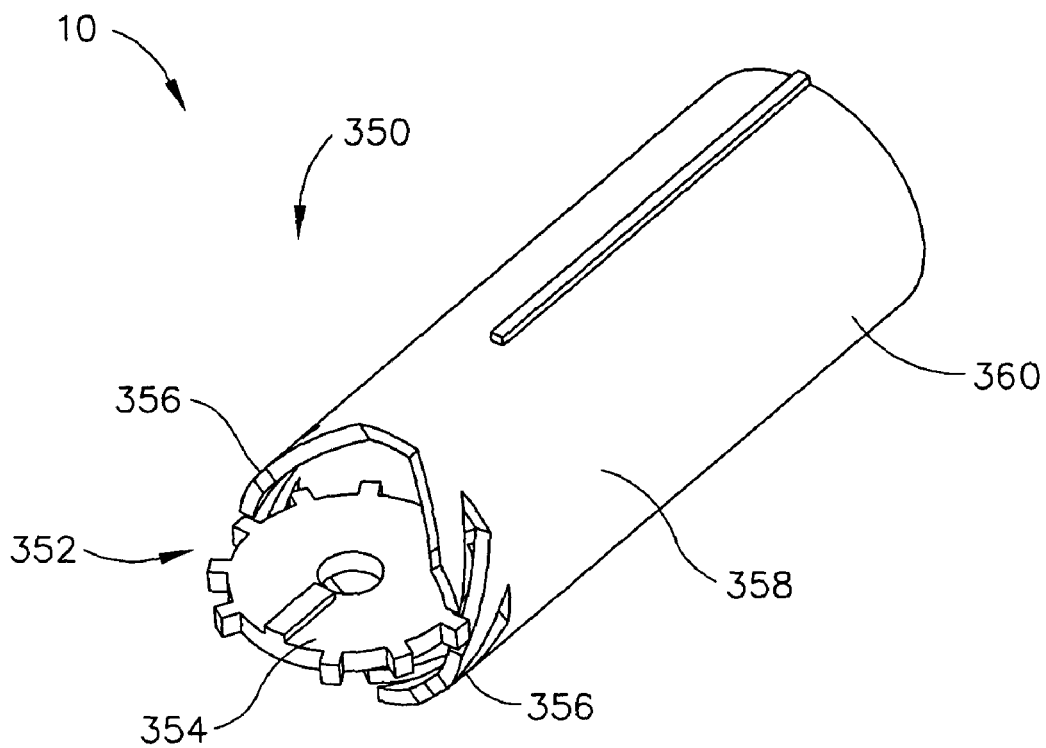
FIG. 12 depicts a front perspective view of a snaggletooth articulation mechanism for the surgical instrument of FIG. 1.
Figure 13:
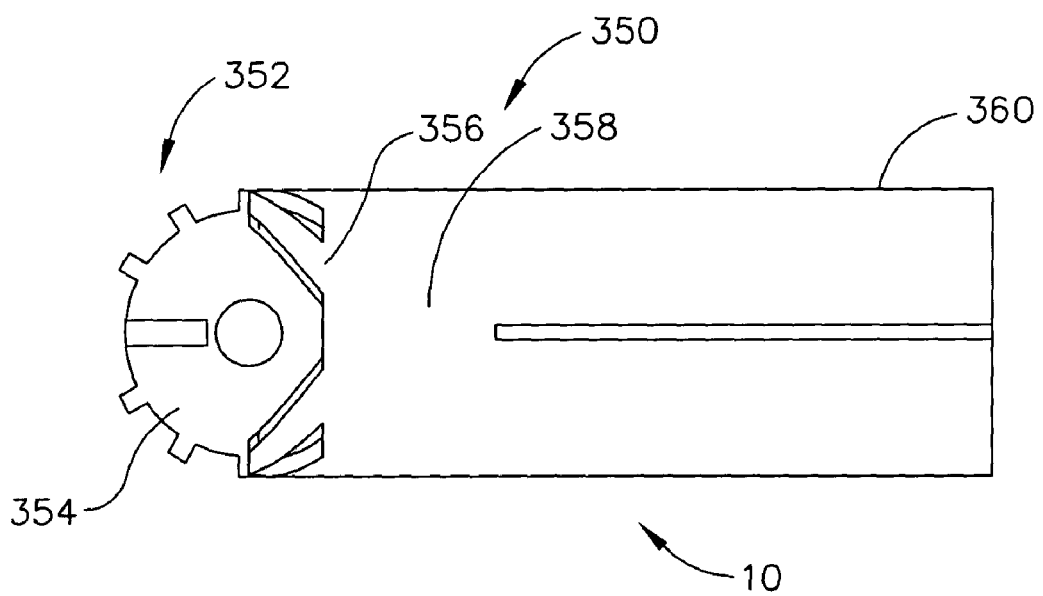
FIG. 13 depicts a top plan view of the snaggle-tooth articulation mechanism of FIG. 12.

FIGS. 12–13 depict an alternative articulation mechanism 350 for the surgical stapling and severing instrument 10 of FIG. 1. A snaggle gear connection 352 is formed therein by positioning a single spur gear 354 of a closure ring 250 (not depicted in FIGS. 12–13) to the longitudinal axis of the closure ring 250. The snaggle gear connection 352 is completed by slanted teeth 356 formed at a distal end 358 of a closure tube 360. Pairs of slanted teeth 356 slope toward each other registered to one side of the spur gear 354 with other pairs of slanted teeth 356 sloping toward the other side of the spur gear 354. This snaggle gear connection 352 achieves a high gear ratio with a relatively large degree of articulation for a given amount of rotation motion about the longitudinal axis by the closure tube 360. It should be appreciated that a various types of interconnections between a shaft and an end effector may be positioned around the articulation mechanism 350 or about each face of the spur gear 354.

Worm Gear Articulation Mechanism

Figure 14:
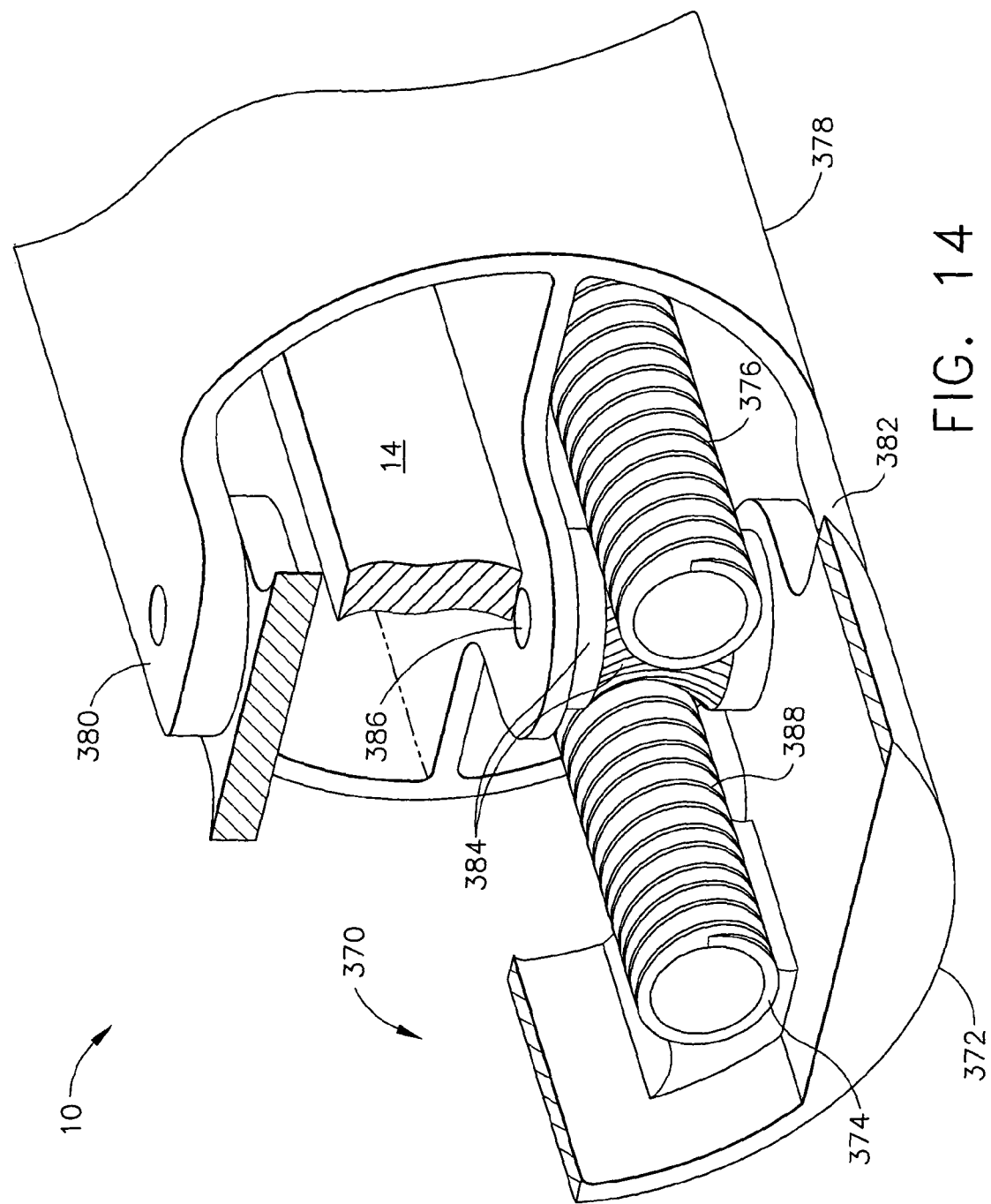
FIG. 14 depicts a front perspective cutaway view of a dual worm-gear articulation mechanism for the surgical instrument of FIG. 1.

FIG. 14 depicts a worm gear articulation mechanism 370 for the surgical stapling and severing instrument 10 of FIG. 1. A closure ring 372 is depicted partially cutaway to expose two articulation 374, 376, each offset laterally from the longitudinal axis of a closure tube 378. The closure ring 372 is pivotally connected at pivot points 380, 382 extending from the closure tube 378, the pivot points 380, 382 defining a pivot axis. A concave face spur gear 384 of hourglass shape is aligned with the pivot axis and attached to the closure ring 372. Concave face spur gear 384 is pivoting about an internal pivot point 386 distally projecting from the closure tube 378. Each articulation drive tube 374, 376 includes worm gear teeth 388 encompassing at least their distal portions that enmesh with opposite sides of the concave face spur gear 384. Thus, by counter-rotating the two articulation drive tubes 374, 376, about the longitudinal axis, the closure ring 372, and thus the end effector 12 (not shown in FIG. 14) is articulated about the pivot axis.

It will be appreciated that only one articulating drive tube 374, 376 may be used. In addition, in application wherein a cavity 390 for a firing bar 14 is not required, it will be appreciated that the concave face spur gear 384 may be centered on the pivot axis rather than offset as depicted. Moreover, although a concave face of hourglass shaped spur gear 384 achieves a large contact area with the articulation drive tubes 374, 376, straight or other shaped faces may be used. Furthermore, the articulation drive tubes 274, 376 may be solid or hollow.

Bevel Gear Articulation Mechanism

Figure 15:
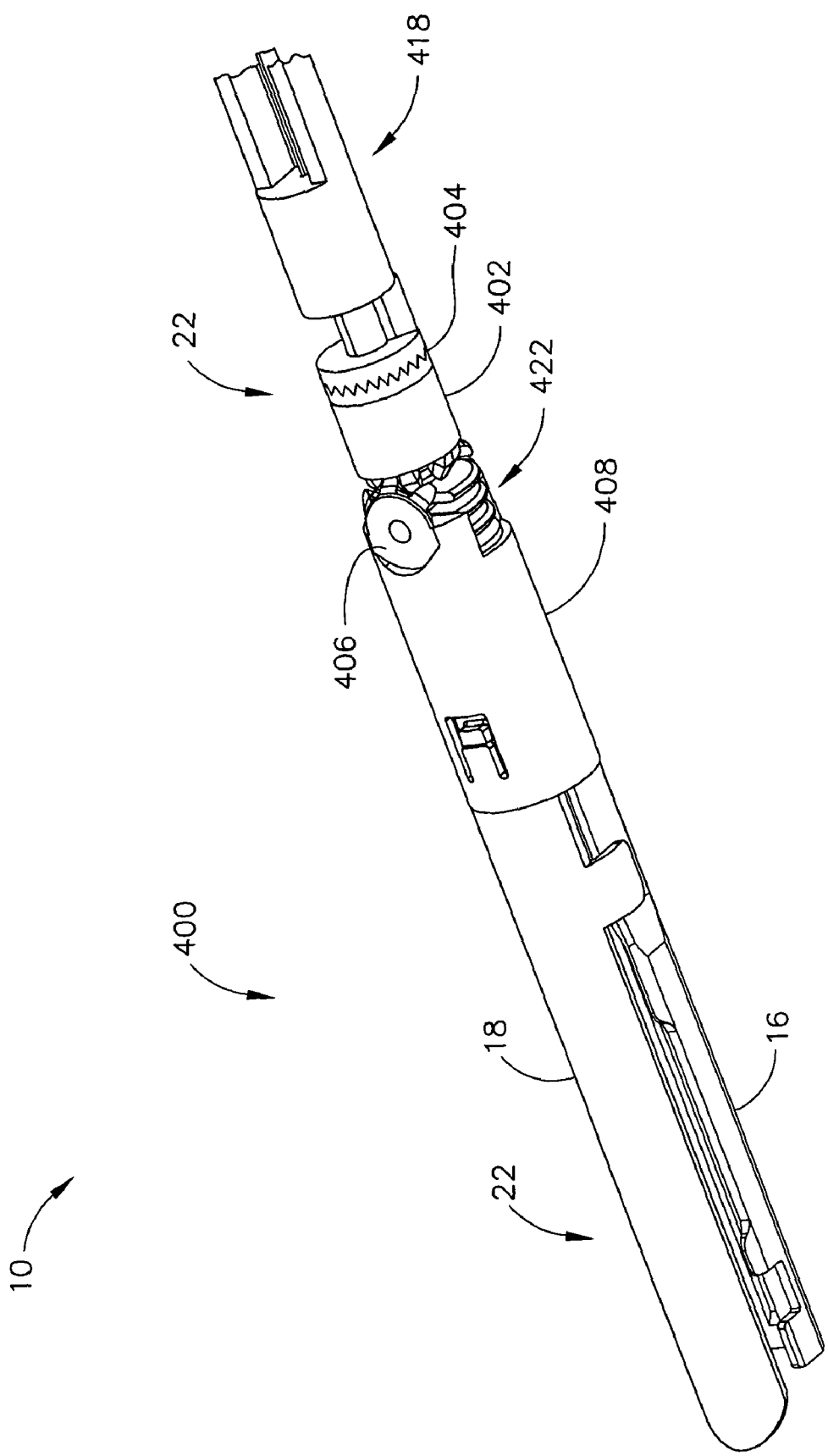
FIG. 15 depicts a side perspective cutaway view of a bevel-gear articulation mechanism for the surgical instrument of FIG. 1.
Figure 16:
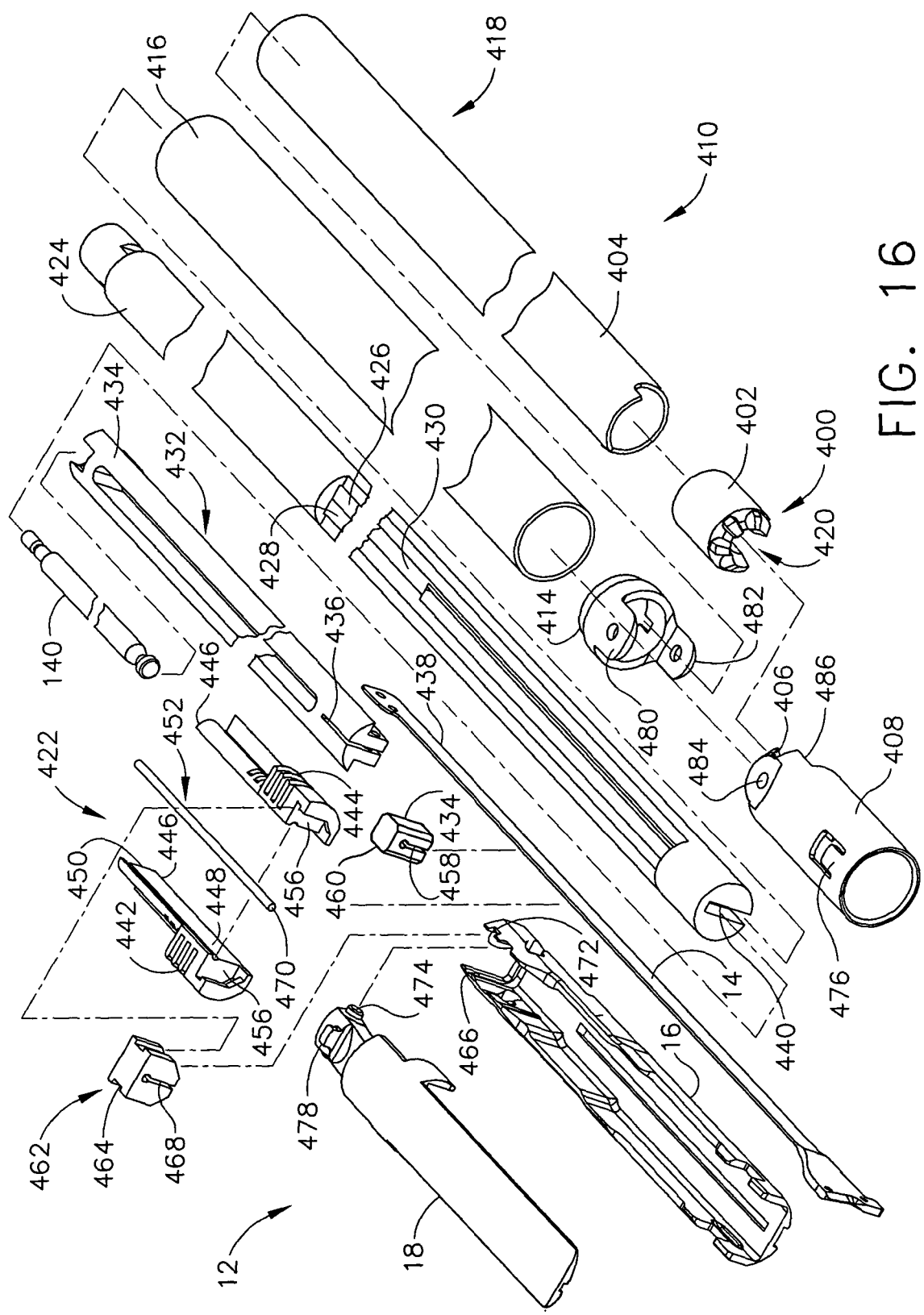
FIG. 16 depicts a perspective, exploded view of an implement portion of the surgical instrument of FIG. 1 including the bevel-gear articulation mechanism of FIG. 15.
Figure 17:
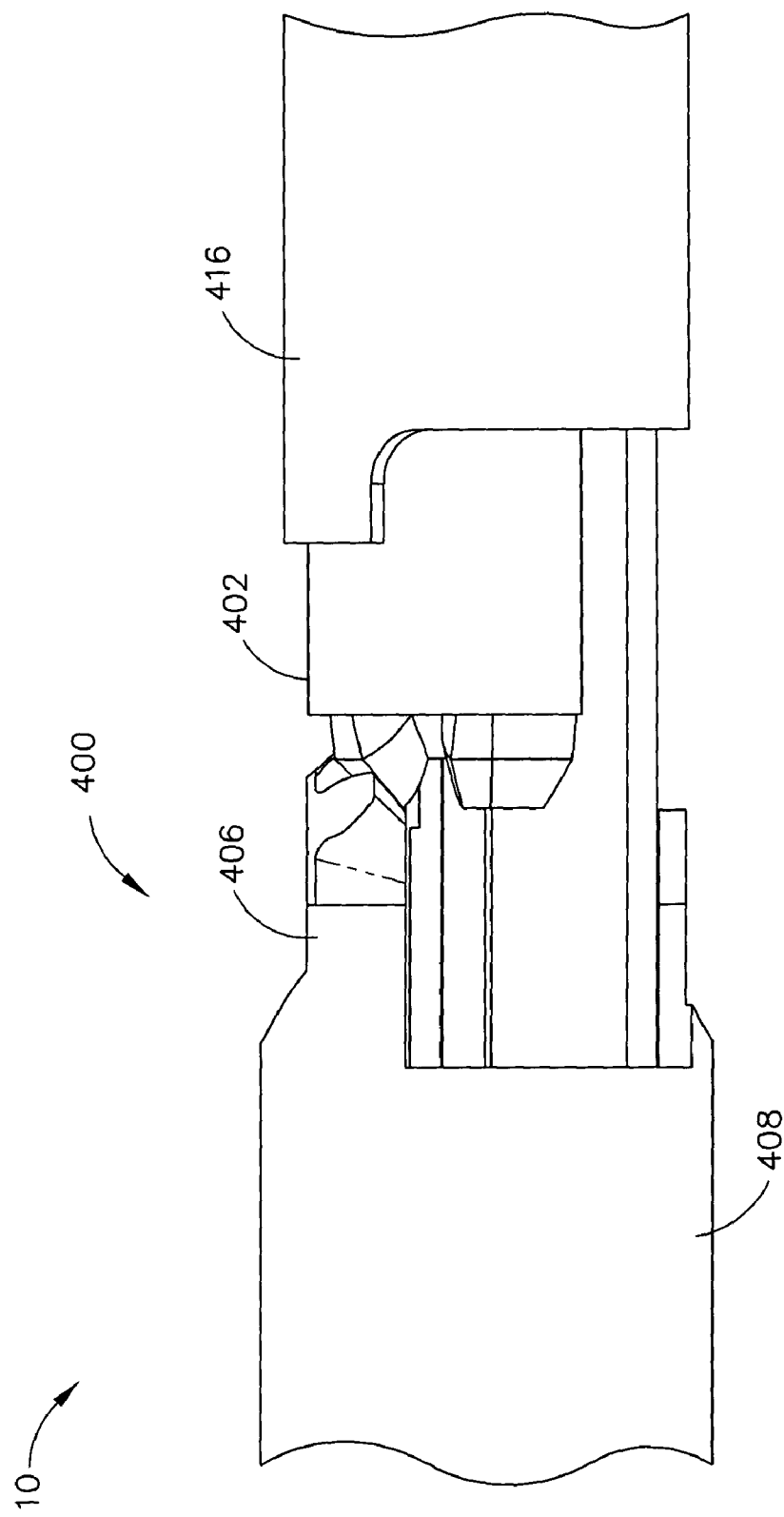
FIG. 17 depicts a side perspective detail view of the bevel-gear articulation mechanism of FIGS. 15–16 partially cutaway to expose closure sleeve, articulation sleeve, and firing portions.

FIGS. 15–17 depict a bevel gear articulation mechanism 400 for the surgical stapling and severing instrument 10 of FIG. 1 that also produces articulation from rotation of a member about the longitudinal axis. Instead of achieving greater strength in the gear connection by inclusion of a reversing gear, snaggle tooth gear, or a worm gear type of connection, a bevel gear section 402 is provided that is coupled to an articulation drive tube 404. In FIG. 15, drive tube 404 is shown sectioned to show elements within. Bevel gear section 402 of tube 404 meshes with a bevel spur gear 406 formed from a closure ring 408.

With particular reference to FIG. 16, an implement portion 410 is depicted having additional advantages, such as the bevel gear articulation mechanism 400 including attachable portions, specifically a pivot connection 414 and the bevel gear section 402, that are not formed respectively into a closure tube 416 or the articulation drive tube 404, thereby simplifying manufacturing processes when facilitating a shaft 418 of selectable lengths. In addition, the assembly of the bevel gear section 402 to a separate articulation drive tube 404 allows for a constriction 420 inside the bevel gear section 402 to be confined to only that portion of the shaft 418 adjacent to bevel gear section 402.

A resilient support section 422 couples a frame 424 distally to the end effector 12 through this constriction 420. A proximal end 426 of the frame 424 is longitudinally positioned to the handle portion 20 (not depicted in FIGS. 15–17) for rotatingly engagement thereto. A frame trough 428 formed by an opening 430 longitudinally aligned along the longitudinal axis of the frame 424 is longer than a firing connector 432 that slides longitudinally within the frame trough 428. A proximal end 434 of the firing connector 432 rotatingly engages the distal end of the metal drive bar 140 (FIG. 6). The distal end of the firing connector 432 includes a slot 436 that receives a proximal end 438 of the firing bar 14, attached therein by pins (not shown).

The more distal portions of the firing bar 14 extend through the frame 424 out through a widened slot 440, guided on each lateral side by the resilient support section 422. In particular, flexible right half and left halves 442, 444 each include a proximal tab 446 that are insertable into the widened slot 440 of the frame 424. Defined into the opposing faces of the two flexible halves 442, 444 of the resilient support section 422 is a firing bar guide 448 and a cylindrical rod recess 450 that receives a flexible rod 452. A rigid guide member 454, which is engaged with a distal recess 456 formed into the distal faces of both flexible halves 442, 444, includes a vertical slot 458 capped by a cylindrical hole 460 longitudinally aligned to receive respectively the firing bar 14 and the flexible rod 452.

An articulating frame member 462 has channel anchoring features 464 that engage an attachment collar 466 of a proximal portion in the elongate channel 16. The firing bar 14 passes through a lower slot 468 in the articulating frame member 462. The articulating frame member 462 is spaced away from the distal end of the resilient support section 422 by being attached to a distal end 470 of the flexible rod 452. Thereby, the elongate channel 16 is attached to the handle portion 20, albeit with a flexible portion for articulation motion therebetween.

The elongate channel 16 also has an anvil cam slot 472 that pivotally receives an anvil pivot 474 of the anvil 18. The closure ring 408 that encompasses the frame 424 includes a distally presented tab 476 that engages an anvil feature 478 proximate but distal to the anvil pivot 474 on the anvil 18 to thereby effect opening and closing of the anvil 18.

The articulation drive tube 404 encompasses the frame 424 and is distally attached to the bevel gear section 402, which in turn encompasses the proximal tabs 446 of the flexible right half and left halves 442, 444. The bevel gear section 402 enmeshes with the bevel spur gear 406 of the closure ring 408, as depicted in FIG. 17. The closure tube 416 is distally attached to the pivot connection 414, which in turn presents distally projecting and laterally opposing tabs 480, 482 that pivotally attach respectively to pivot points 484, 486 of the closure ring 408.

Flex-neck Articulation Mechanism

Figure 18:
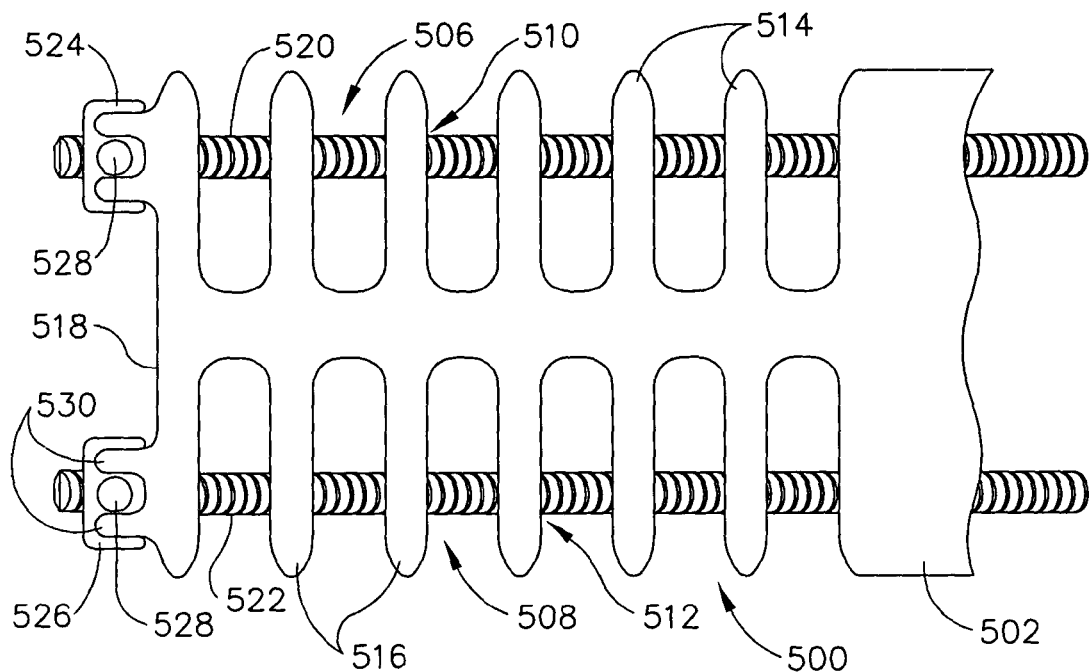
FIG. 18 depicts a top view of a dual rod flex-neck articulation mechanism for the surgical instrument of FIG. 1.
Figure 19:
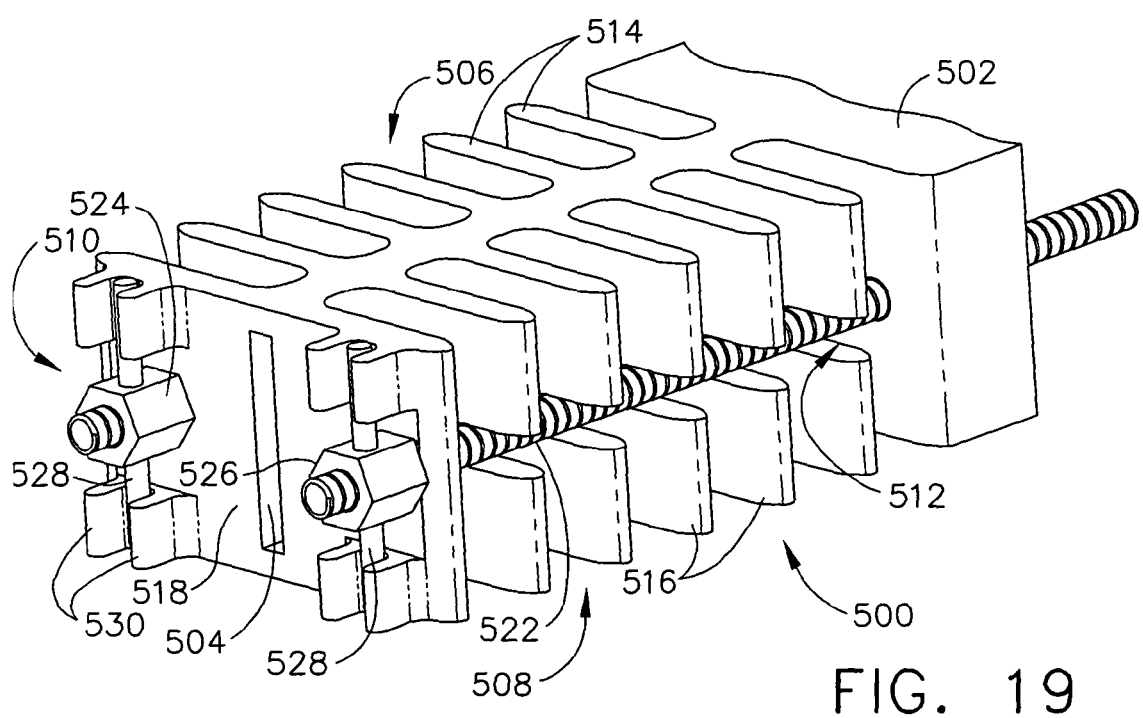
FIG. 19 depicts a front perspective view of the dual rod flex-neck articulation mechanism of FIG. 18.

FIGS. 18–19 depict a flex-neck articulation mechanism 500 for the surgical instrument 10 of FIG. 1 that also employs a rotational articulation motion about the longitudinal axis to effect the articulation of an end effector 12 (not depicted in FIGS. 18–19). Unlike known flex-neck articulation mechanism, the rotation articulation motion provides a smooth and continuous positioning capability.

In particular, a resilient flex-neck body 502 includes a firing bar slot 504 through its longitudinal axis to receive the firing bar 14 (not depicted in FIGS. 18–19). A series of parallel right-hand and left-hand slots 506, 508 projecting inward in opposite direction into the flex-neck body 502 enable articulation to the left and right, perpendicular to the firing bar slot 504. Right-hand and left-hand cylindrical passages 510, 512 are offset from the longitudinal axis of the flex-neck body 502 and are formed respectively into the resulting right-hand and left-hand fins 514, 516 formed by the right-hand and left-hand slots 506, 508.

A distal face 518 of the flex-neck body 502 is located at the most distal of the right-hand and left-hand fins 510, 512. Distal face 518 includes gear connection capabilities to convert the rotational articulation motion of right-hand and left-hand articulation tubes, depicted as threaded rods 520, 522, into an articulation motion. Specifically, threaded nuts 524, 526 are attached to each side respectively on the distal face 518. In the illustrative version, each threaded nut 524, 526 includes a pair of laterally projecting pins 528 that snap respectively into gripping fingers 530 to prevent rotation of threaded nuts 524,526. When the threaded nuts 524,526 are threaded in the same direction, such as left hand or right hand threads, the threaded rods 520 and 522 must be rotated in opposite directions to articulate the flex neck body 502. As threaded rods 520, 522 are rotated in opposite directions, one nut 524, 526 moves proximally and one nut 524,526 moves distally. The proximally moving nut 524 or 526 shortens the portion of the threaded rod 516, 518 proximal to the threaded nut 524, 526, thus compressing the corresponding right-hand or left-hand slots 506, 508.

Operation

A closed end effector 12 and shaft 23 of an implement portion 22 of a surgical stapling and severing instrument 10 are inserted through a cannula passageway of a trocar to a surgical site for an endoscopic or laparoscopic procedure. The articulation control 13 is rotated as desired about the longitudinal axis of the shaft 23 to effect a corresponding rotation of the end effector 12. Advantageously, the actuator lever 202 of the articulation control 13 is pivoted to create a rotation articulation motion about the longitudinal axis of surgical instrument 10 in an articulation drive tube 200, 242, 374, 520 that is converted into an articulation motion at a geared connection in an articulation mechanism 11, 240, 370, 400, 500, thereby positioning the end effector 12 in a desired position.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, the present invention has been discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

For another example, although the E-beam firing beam 14 has advantages for an endoscopically employed surgical severing and stapling instrument 10, a similar E-beam may be used in other clinical procedures. It is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

For yet another example, although an illustrative handle portion 20 described herein is manually operated by a clinician, it is consistent with aspects of the invention for some or all of the functions of a handle portion to be powered (e.g., pneumatic, hydraulic, electromechanical, ultrasonic, etc.). Furthermore, controls of each of these functions may be manually presented on a handle portion or be remotely controlled (e.g., wireless remote, automated remote console, etc.).

As yet an additional example, although a simultaneous stapling and severing instrument is advantageously illustrated herein, it would be consistent with aspects of the invention rotationally controlled articulation with other types of end effectors, such as grasper, cutter, staplers, clip applier, access device, drug/gene therapy delivery device, and a energy device using ultrasound, RF, laser, etc.

What is claimed is:

1. A surgical instrument, comprising:
    a shaft comprising a frame, a firing member supported by the frame configured to transfer an actuating motion, and comprising an articulation drive tube encompassing the frame and firing member and configured to transfer a rotational motion about a longitudinal axis thereof;
    a handle portion proximally attached to the frame and coupled to the shaft operably configured to produce the actuating motion and the rotational motion;
    an end effector distally, pivotally attached to the frame for lateral articulation about a pivot axis perpendicular to the longitudinal axis of the frame; and
    a gear train articulation mechanism responsive to the rotational motion to articulate the end effector, comprising:
        a spur gear attached to the end effector and aligned in an arc proximal to and equidistant from the perpendicular pivot axis of the pivotal coupling of the end effector, and
        a gear section presented about at least a portion of a distal end of the articulation drive tube communicating the rotational motion to the spur gear of the pivotal coupling of the end effector.

2. The surgical instrument of claim 1, wherein the end effector comprises a stapling and severing mechanism, wherein the actuating motion comprising a longitudinal firing motion and the stapling and severing mechanism is further responsive to a longitudinal closing motion, the handle portion and shaft configured to produce and transfer the firing and closing motions.

3. The surgical instrument of claim 2, wherein the shaft includes a closure member responsive to the longitudinal closing motion and pivotally coupled to the end effector, the shaft further includes a firing bar and the frame supporting the firing bar configured to transfer the firing motion to the end effector.

4. The surgical instrument of claim 1, wherein the pivotal attachment at the pivot axis comprises a pair of distally projecting, laterally opposed posts extending from the frame respectively coupled to a pair of proximally projecting, laterally opposed pivot points extending from the end effector.

5. The surgical instrument of claim 1,
    wherein the shaft further comprises an articulation drive tube responsive to the rotational motion from the handle portion and distally terminating in a gear section, the articulation mechanism comprising a spur gear proximally attached to the end effector and engaged by the gear section;
    wherein the articulation drive tube further comprises a second gear section proximally recessed with respect to the first gear section, the end effector further comprises a proximally projecting gear section laterally opposite the spur gear, the surgical instrument further comprising a reversing gear engaged between the second gear section and the proximally projecting gear section.

6. The surgical instrument of claim 1, wherein the gear section and the spur gear form a bevel gear connection.

7. The surgical instrument of claim 1, wherein the spur gear is aligned with the longitudinal axis of the frame presenting gear teeth to each lateral side of the articulation drive tube, the first gear section of the articulation drive tube positioned on one lateral side comprising a plurality of slanted snaggle teeth engaging gear teeth on one lateral side of the spur gear, further comprising a second gear section of the articulation drive tube opposite to the first gear section comprised of a plurality of oppositely slanted snaggle teeth engaging corresponding gear teeth on the other lateral side of the spur gear.

8. A surgical instrument, comprising:
- a handle portion operably configured to produce a rotational motion;
- a shaft having a longitudinal axis and comprising:
  - an elongate frame attached to the handle portion and defining a longitudinal axis,
  - an articulation drive tube encompassing the elongate frame and responsive to the rotational motion, and
  - a gear section distally projecting about at least a portion of a circumference of a distal end of the articulation drive tube;
- an end effector pivotally coupled to the shaft at a pivot axis perpendicular to the longitudinal axis; and
- a spur gear on the pivot axis, proximally attached to the end effector and engaged to the gear section to convert the rotational motion of the articulation drive tube to an articulation motion pivoting the end effector in a lateral arcing movement;
- wherein the articulation drive tube further comprises a second gear section proximally recessed with respect to the first gear section, the end effector further comprises a proximally projecting gear section laterally opposite the spur gear, the surgical instrument further comprising a reversing gear engaged between the second gear section and the proximally projecting gear section.

* * * * *